United States Patent
Yang et al.

(10) Patent No.: US 7,640,681 B2
(45) Date of Patent: Jan. 5, 2010

(54) ELECTRIC MASSAGE SHOE ASSEMBLY

(76) Inventors: Li-Hua Yang, No. 89, Dongying 13th St., East District, Taichung City 401 (TW); Chia-Na Ho, No. 57, Sec. 2, Jhongsing Rd., Dali City, Taichung County 412 (TW)

( * ) Notice: Subject to any disclaimer, the term of this patent is extended or adjusted under 35 U.S.C. 154(b) by 567 days.

(21) Appl. No.: 11/633,609

(22) Filed: Dec. 4, 2006

(65) Prior Publication Data

US 2008/0132811 A1    Jun. 5, 2008

(51) Int. Cl.
*A61F 5/14* (2006.01)
(52) U.S. Cl. .......................................... 36/141
(58) Field of Classification Search ............... 36/43, 36/140, 141
See application file for complete search history.

(56) References Cited

U.S. PATENT DOCUMENTS

| 7,210,253 | B2 * | 5/2007 | Yu .............................. 36/141 |
| 7,487,606 | B2 * | 2/2009 | Koo et al. ...................... 36/141 |
| 2006/0185196 | A1 * | 8/2006 | Wang ........................... 36/141 |
| 2008/0066343 | A1 * | 3/2008 | Sanabria-Hernandez ....... 36/43 |

* cited by examiner

*Primary Examiner*—Marie Patterson
(74) *Attorney, Agent, or Firm*—Charles E. Baxley (57) ABSTRACT

An electric massage shoe assembly includes a shoe with a conductive unit received therein which has a receptacle, a first wire and at least one conductive rod which extends through an insole unit and is in contact with wearer's foot. A frequency current generating unit is electrically connected to the receptacle of the conductive unit so as to transfer frequency current to the wearer's foot and stimulate the wearer's foot.

11 Claims, 9 Drawing Sheets

ELECTRIC MASSAGE SHOE ASSEMBLY

FIELD OF THE INVENTION

The present invention relates to an electric massage shoe assembly and each shoe includes a conductive insole powered by a power supply set so as to provide vibration at different points to the wearer's feet.

BACKGROUND OF THE INVENTION

A conventional way to massage the feet is to walk or stand on a pad on which a plurality of bosses protrude, the bosses stimulate the reflecting points of the feet to improve the blood circulation and even stimulate different parts of user's body. Nevertheless, a common experience is that the bosses really hurt the feet because they are stiff. If the sizes of the bosses are reduced or are made softer, the massage result is reduced.

Figure 9:
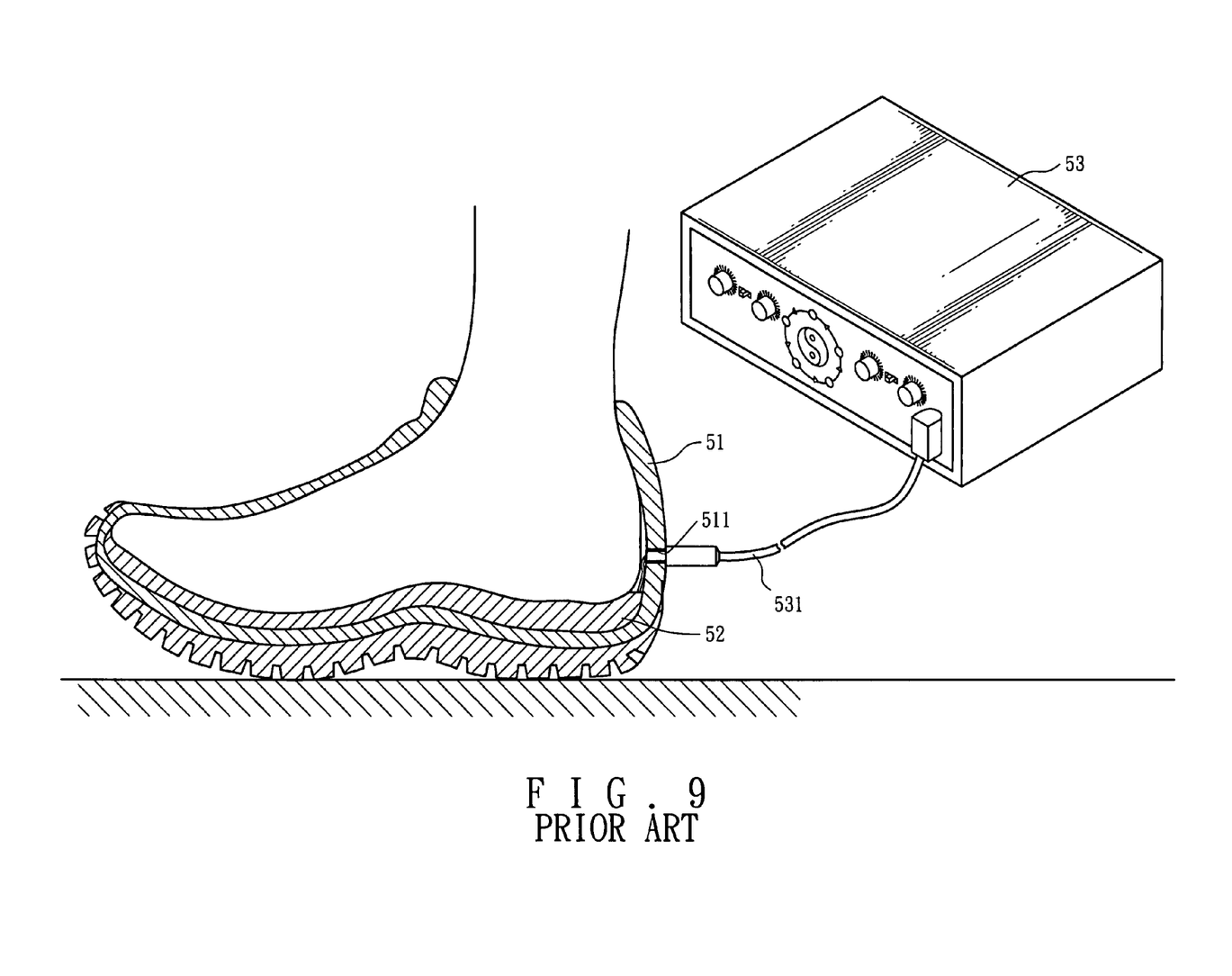
FIG. 9 shows a conventional electric massage shoe assembly.

A conventional electric massage shoe assembly 50 is shown in FIG. 9 and generally includes a shoe having an insole 52 received therein and a receptacle 511 is defined through the counter 51 of the shoe. A power supply set 53 is provided which has a cable 531 connected thereto and an end of the cable 531 is plugged into the receptacle 511 so as to electrically connect the conductive wire in the shoe. The insole 52 is a solid plate with a plurality of bosses on a top surface thereof which is in contact with the wearer's foot. The bosses are connected with the wire so that the electricity stimulates the wearer's foot when the power supply set 53 is set to "ON" so as to have massage feature.

However, the solid insole 52 is stiff so that the wearer cannot feel comfortable after standing for a period of time. Besides, the power supply set 53 is not convenient for carrying and the length of the cable 531 limits the convenience of the use of the massage shoe assembly 50.

The present invention intends to provide electric massage shoes wherein the power supply set is compact and easily to carry so as to provide adjustable vibration to the wearer's feet.

SUMMARY OF THE INVENTION

The present invention relates to an electric massage shoe assembly which comprises a shoe and a conductive unit is received in the shoe. The conductive unit has a receptacle, at least one conductive rod and a first wire connected between the receptacle and the at least one conductive rod. An insole unit is received in the shoe and includes a first part and a second part which is overlapped on the first part. The at least one conductive rod extends through a through hole defined through the first part and is in contact with wearer's foot. A frequency current generating unit has two plugs, a frequency current generating member and two second wires connected between the two plugs and the frequency current generating member. One of the two plugs is connected with the receptacle.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Referring to FIGS. 1 to 4, the first embodiment of the electric massage shoe assembly of the present invention comprises a pair of shoes 10 and an aperture 11 is defined through a heel portion 100 of each of the shoes 10. A conductive unit 20 is received in the shoe 10 and includes a receptacle 21, a first wire 22 and at least one conductive rod 24, wherein the first wire 22 connected between the receptacle 21 and the at least one conductive rod 24. The conductive rod 24 is connected on a top of a conductive plate 23 which is connected to the first wire 22 and located opposite the receptacle 21. The at least one conductive rod 24 and the conductive plate 23 are made by flexible conductive material such as conductive silicone, conductive rubber, conductive fabric or conductive metal sheet. The receptacle 21 of the conductive unit 20 is inserted in the aperture 11. A groove 12 is defined the inside of the shoe 10 and communicates with the aperture 11. The first wire 22 is received in the groove 12 and the receptacle 21 is inserted in the aperture 11.

An insole unit 30 is received in the shoe 10 and has a first part 31 and a second part 33 which is overlapped on the first part 31. The first part 31 is made by foam material or soft rubber. The conductive unit 20 is located between the first part 31 and an inside of the shoe 10. A through hole 311 is defined through the first part 31 and the at least one conductive rod 24 extends through the through hole 311. A conductive mediate part 32 can be located between the first and second parts 31, 33. The conductive mediate part 32 is in contact with the conductive rod 24 and includes a plurality of protrusions 321 on a top thereof. The second part 33 includes a plurality of holes 331 through which the protrusions 321 extend so as to contact the wearer's feet.

A frequency current generating unit 40 has two plugs 41, a frequency current generating member 43 and two second wires 42 connected between the two plugs 41 and the frequency current generating member 43. The two plugs 41 are respectively connected with the two receptacles 21 of the two shoes 10. The frequency current generated by the frequency current generating unit 40 is transferred to the metal mediate parts 32 in the two shoes 10 so as to stimulate the wearer's feet via the protrusions 321. The frequency can be adjusted by the wearer when needed. The frequency current generating unit 40 is compact and portable so that the wearer can normally walks or even go jogging while the massage function is in operation.

Figure 1:
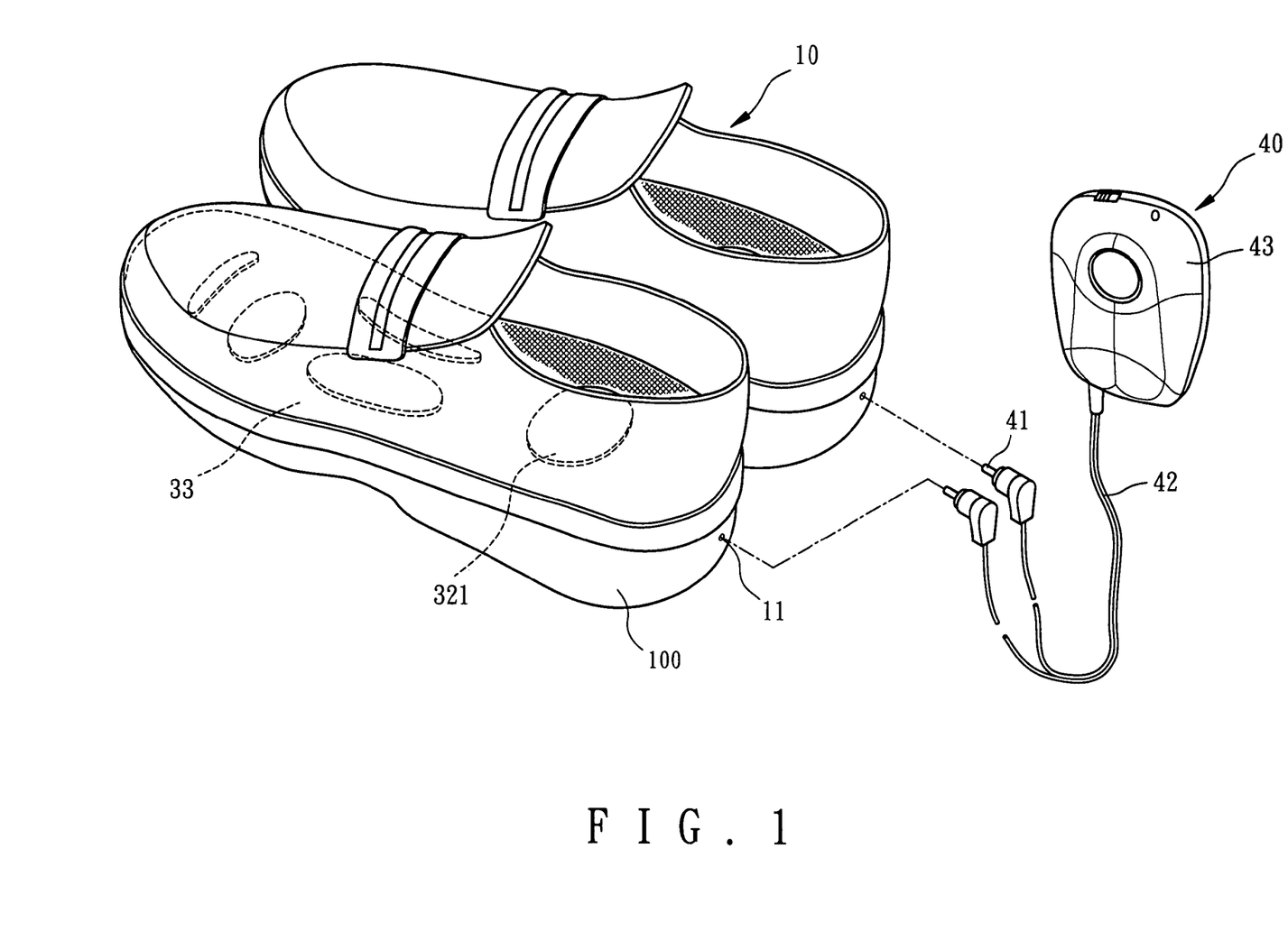
FIG. 1 shows the shoes and the frequency current generating unit of a first embodiment of the electric massage shoe assembly of the present invention.
Figure 2:
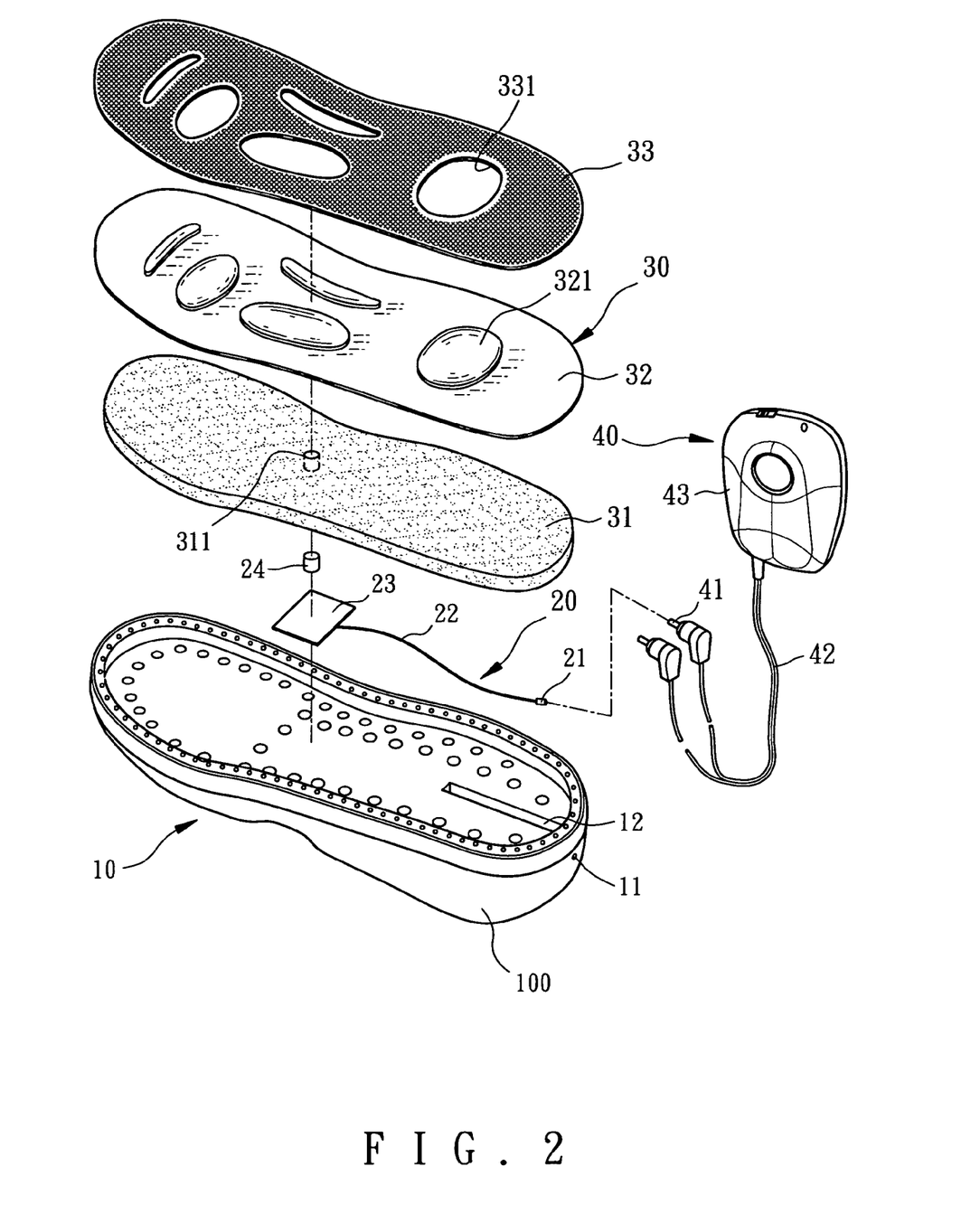
FIG. 2 is an exploded view to show the first embodiment of the electric massage shoe assembly of the present invention.
Figure 3:
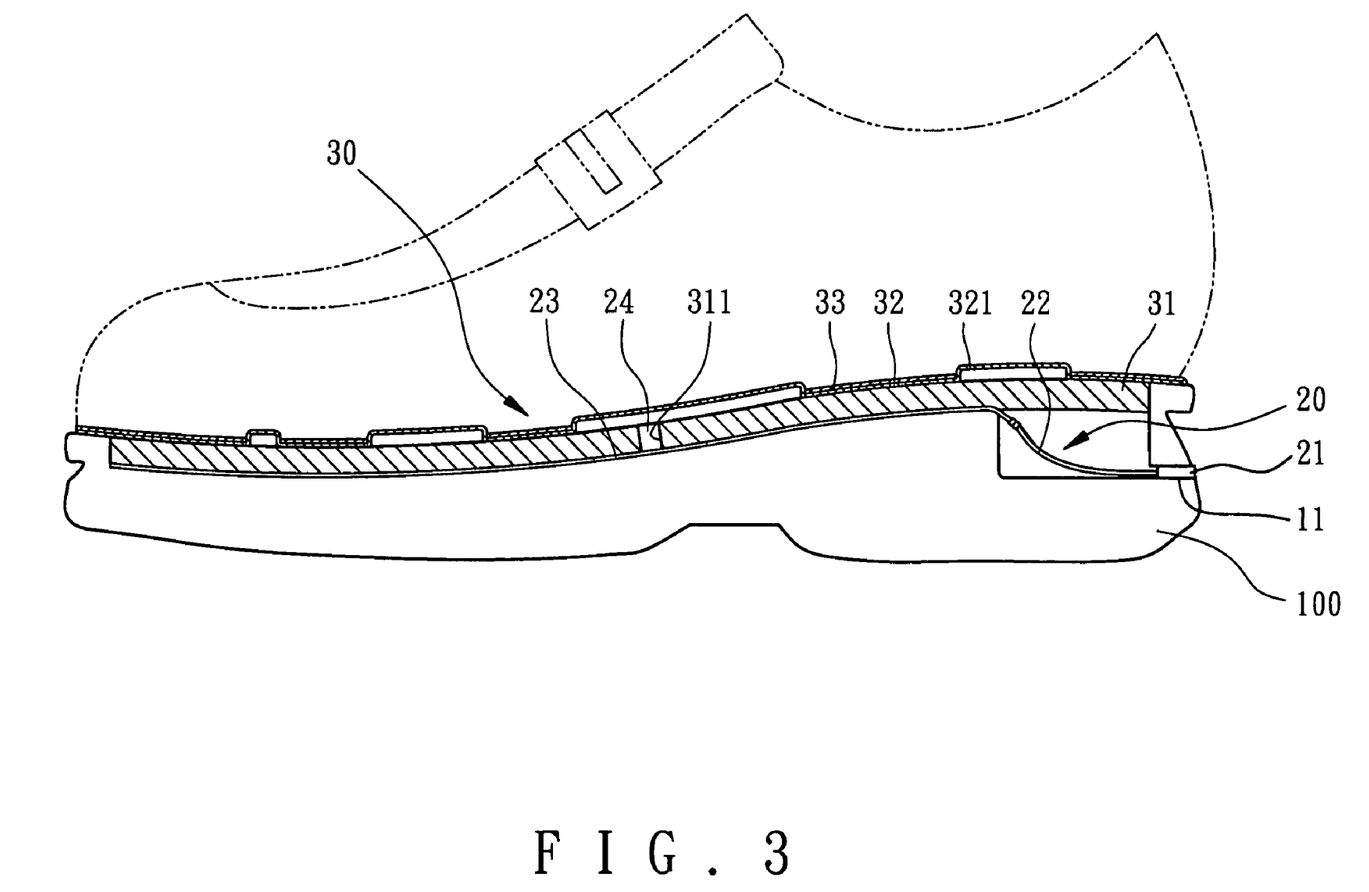
FIG. 3 is a side cross sectional view of the electric massage shoe assembly of the present invention.
Figure 4:
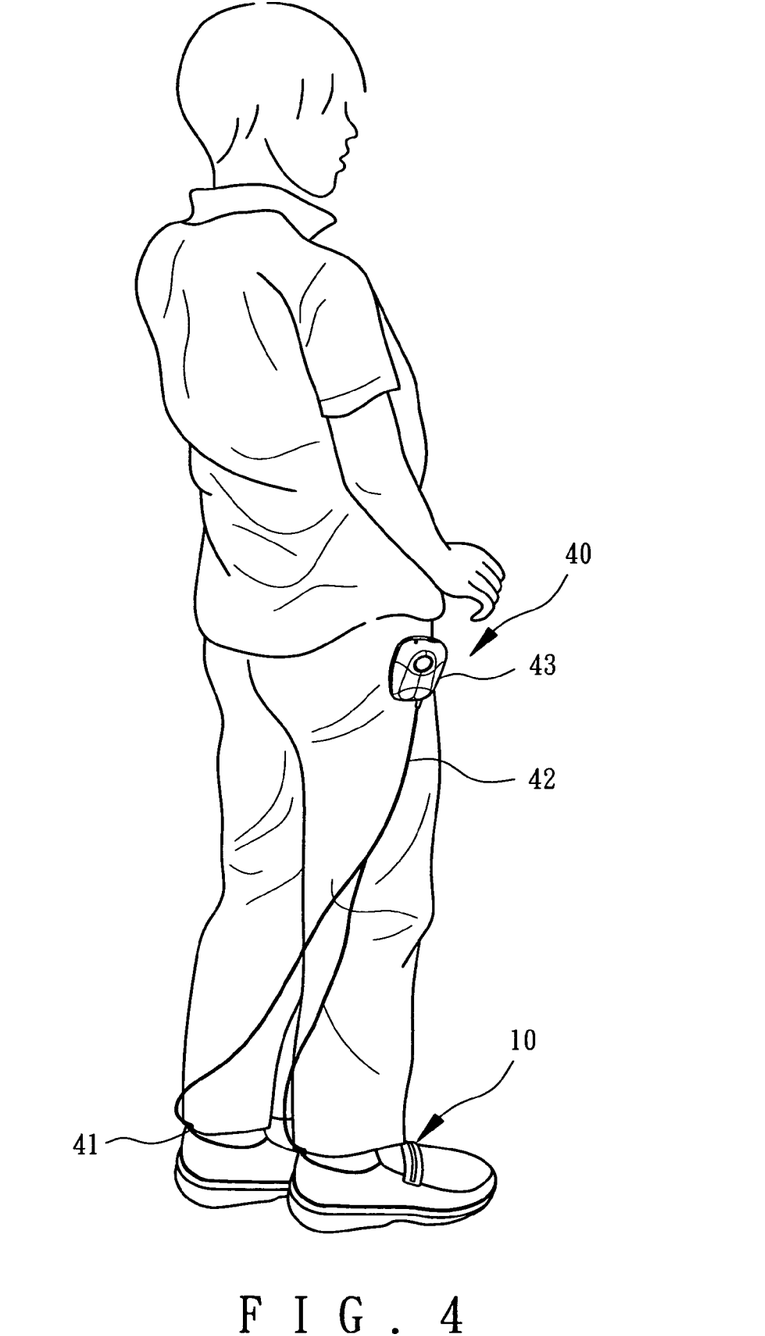
FIG. 4 shows a wearer uses the electric massage shoe assembly of the present invention.
Figure 5:
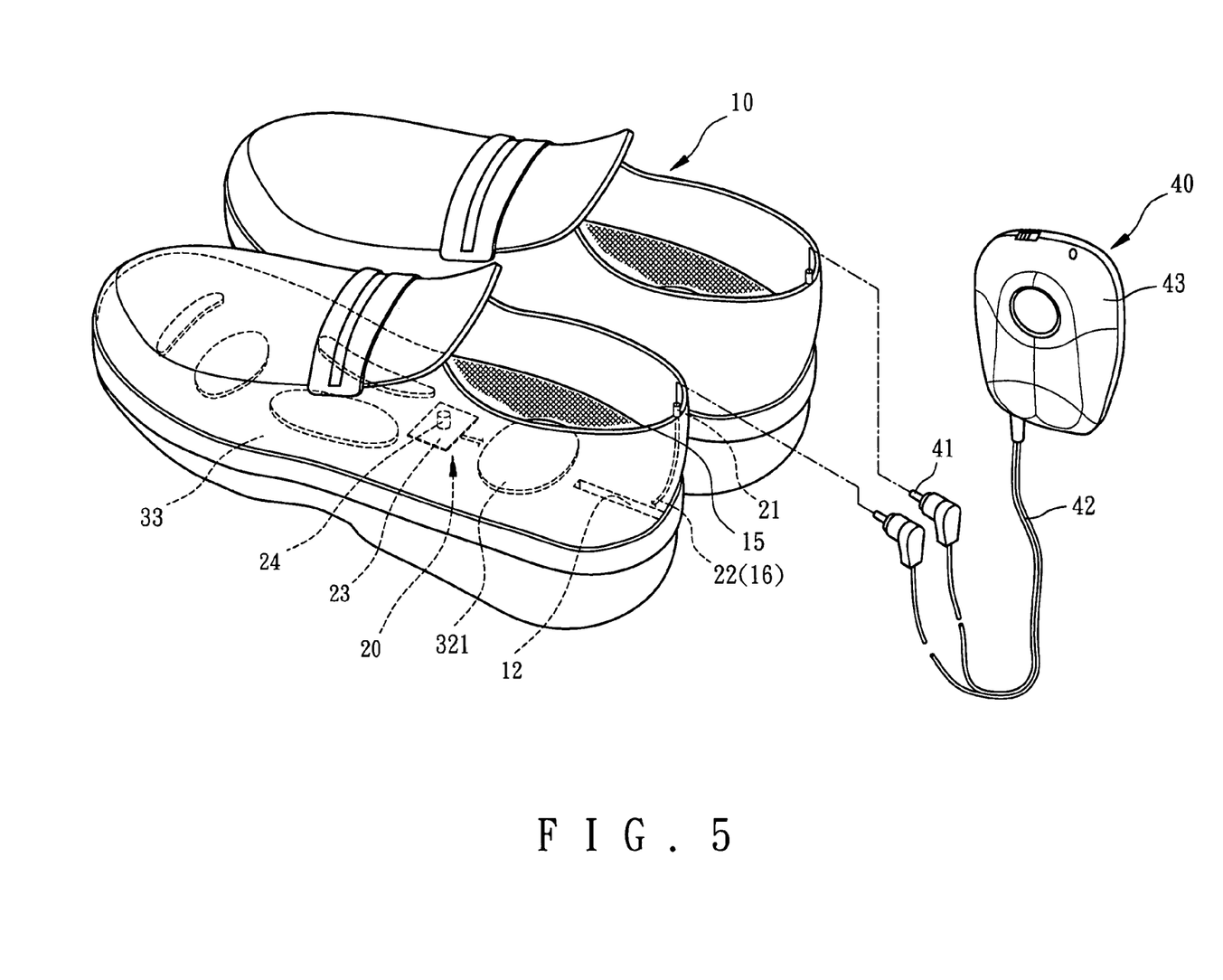
FIG. 5 shows the shoes and the frequency current generating unit of a second embodiment of the electric massage shoe assembly of the present invention.

FIG. 5 shows the second embodiment of the electric massage shoe assembly of the present invention, wherein a recessed path 16 is vertically defined in an inside of a counter 15 of the shoe 10 and a groove 12 is defined the inside of the shoe 10 and communicates with the recessed path 16. The first wires 22 are received in the groove 12 and the recessed path 16, the receptacle 21 is located in the recessed path 16 and on a top edge of the counter 15. Therefore, the plugs 14 are vertically inserted into the receptacles 21 and will not be tangled by foreign objects during walking.

Figure 6:
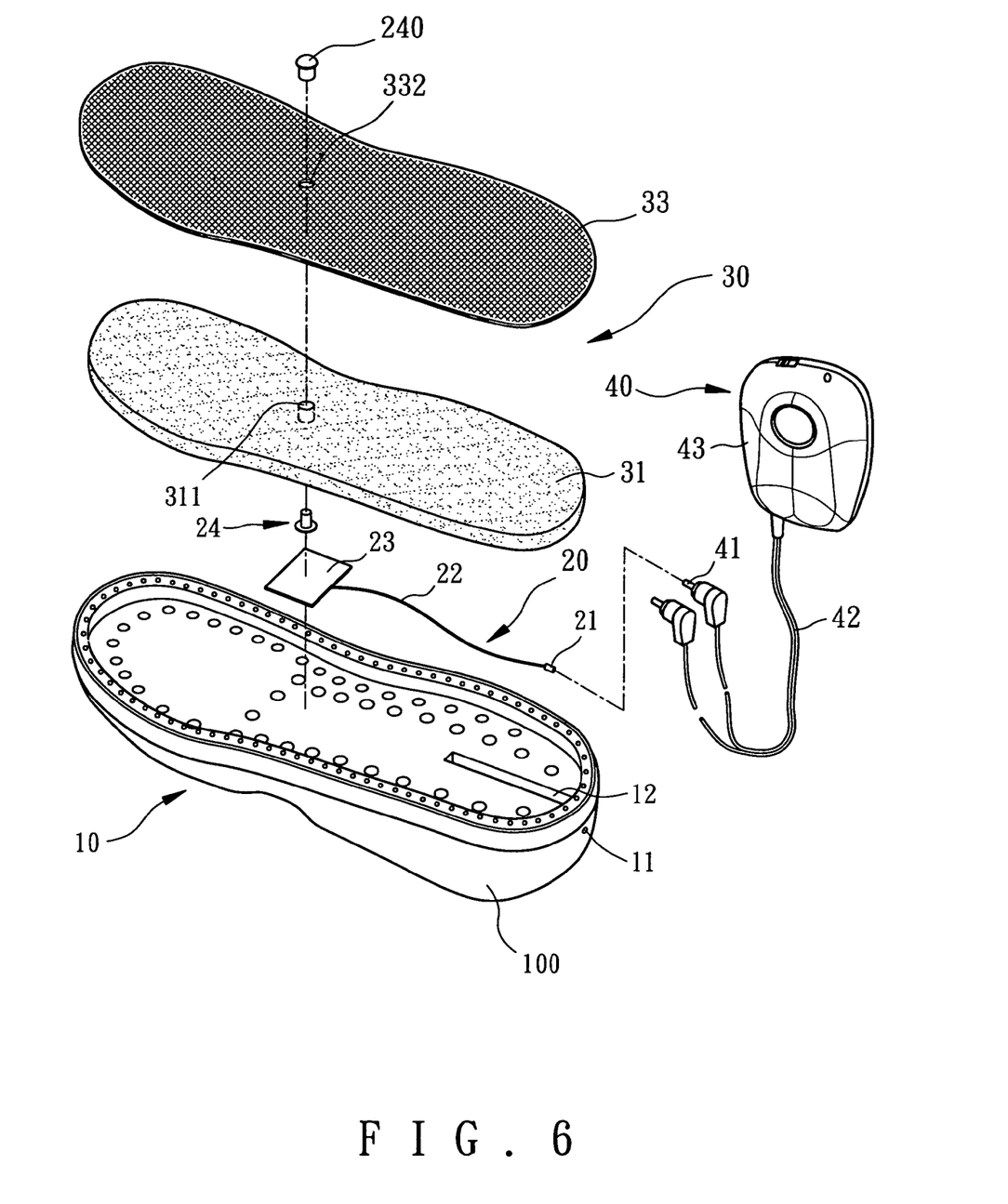
FIG. 6 is an exploded view to show a third embodiment of the electric massage shoe assembly of the present invention.

FIG. 6 shows the third embodiment of the electric massage shoe assembly of the present invention, wherein the aperture 11 is defined through the heel portion 100 of each shoe 10. The conductive rod 24 is composed of two portions which are securely connected to each other as a rivet.

Figure 7:
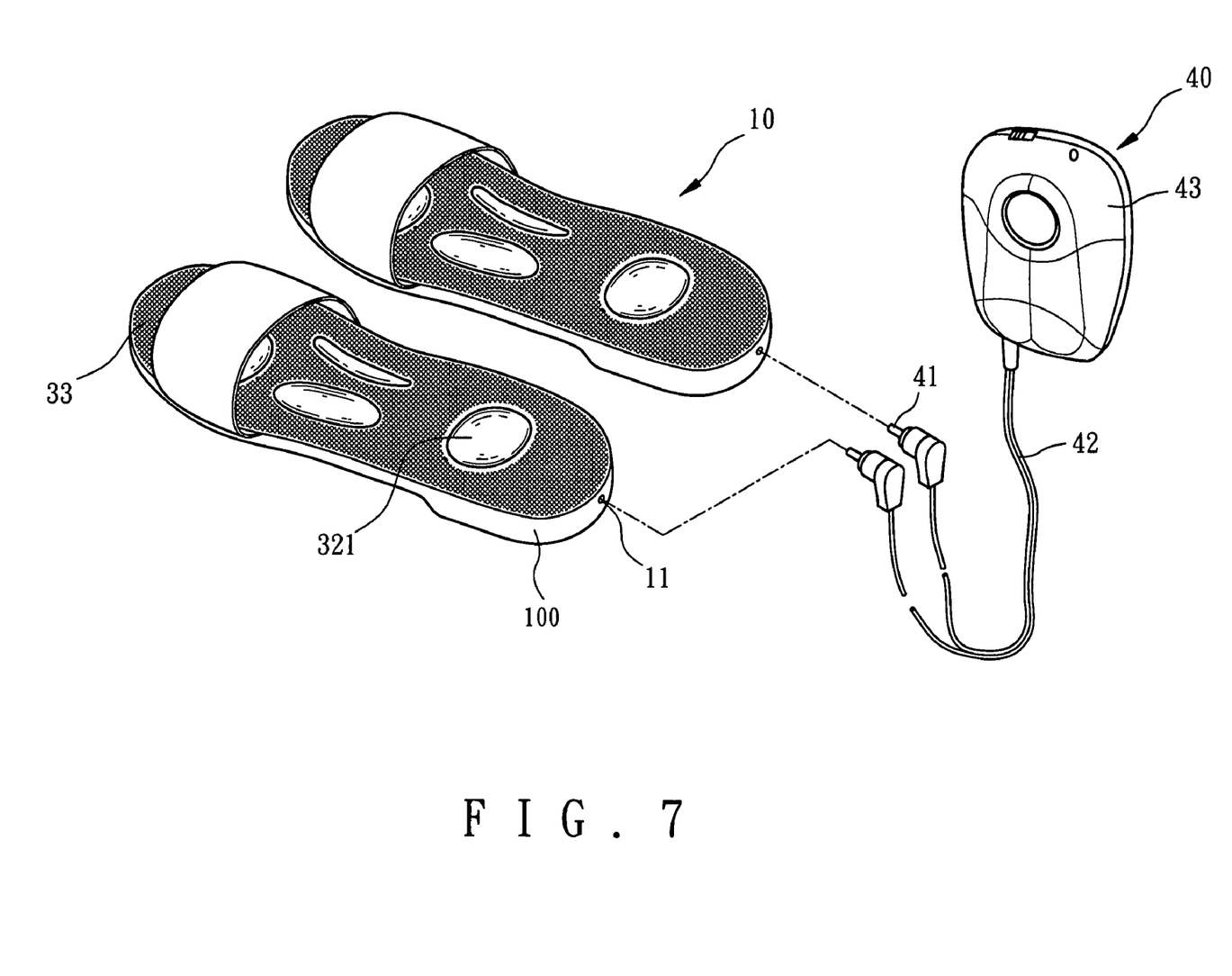
FIG. 7 shows that the electric massage shoe assembly of the present invention is cooperated with a pair of slippers.

FIG. 7 shows that the electric massage shoe assembly of the present invention can also be cooperated with a pair of slippers with the aperture 11 defined in the heel portion 100. The slippers each have the insole unit 30 and only the second part 33 and the protrusions 321 are seen in FIG. 7.

Figure 8:
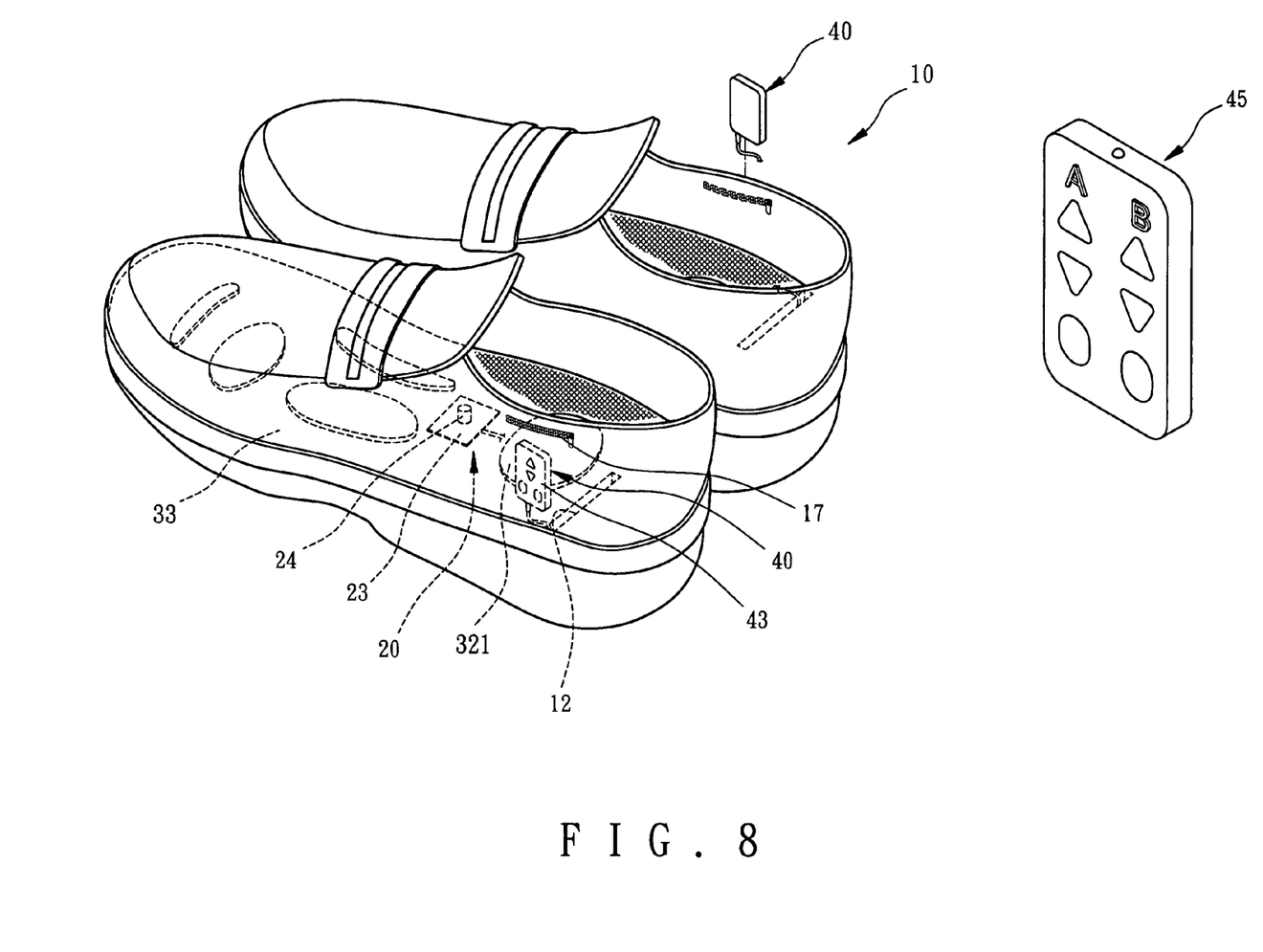
FIG. 8 shows the shoes and the frequency current generating unit of a fourth embodiment of the electric massage shoe assembly of the present invention.

FIG. 8 shows a fourth embodiment of the electric massage shoe assembly of the present invention wherein each shoe 10 has a pocket 17 defined therein which can be sealed by a zipper and two frequency current generating unit 40 are respectively received in the two pockets 17 of the shoes 10 so as to respectively activate the conductive units 20 in the two shoes 10. The insole unit 30 in each shoe 10 is the same as the FIG. 2. The frequency current generating unit 40 is controlled by a remote control 45, therefore no connecting wires are necessary and thus provides more flexibility for wearers while moving.

While we have shown and described the embodiment in accordance with the present invention, it should be clear to those skilled in the art that further embodiments may be made without departing from the scope of the present invention.

What is claimed is:

1. An electric massage shoe assembly comprising:
   a shoe;
   a conductive unit received in the shoe and having a receptacle, a first wire and at least one conductive rod, the first wire connected between the receptacle and the at least one conductive rod;
   an insole unit received in the shoe and having a first part and a second part which is overlapped on the first part, the conductive unit located between the first part and an inside of the shoe, a through hole defined through the first part and the at least one conductive rod extending through the through hole, and
   a frequency current generating unit having two plugs, a frequency current generating member and two second wires connected between the two plugs and the frequency current generating member, one of the two plugs connected with the receptacle.

2. The assembly as claimed in claim 1, wherein an aperture is defined through a heel portion of the shoe and the receptacle of the conductive unit is inserted in the aperture, a groove is defined the inside of the shoe and communicates with the aperture so that the first wire is received in the groove.

3. The assembly as claimed in claim 1, wherein a recessed path is defined in an inside of a counter of the shoe and a groove is defined the inside of the shoe and communicates with the recessed path so that the first wires are received in the groove and the recessed path, the receptacle of the conductive unit is located on a top edge of the counter.

4. The assembly as claimed in claim 1, wherein the at least one conductive rod is connected on a top of a conductive plate which is connected to the first wire and located opposite the receptacle.

5. The assembly as claimed in claim 1, wherein the conductive rod is made by flexible conductive material.

6. The assembly as claimed in claim 4, wherein the conductive plate is made by flexible conductive material.

7. The assembly as claimed in claim 1, wherein a conductive mediate part is located between the first and second parts, the conductive mediate part is in contact with the conductive rod and includes a plurality of protrusions on a top thereof, the second part includes a plurality of holes through which the protrusions extend.

8. The assembly as claimed in claim 1, wherein the first part is made by foam material.

9. The assembly as claimed in claim 1, wherein the conductive rod is composed of two portions which are securely connected to each other.

10. An electric massage shoe assembly comprising:
    a shoe having a pocket defined therein;
    a conductive unit received in the shoe and having at least one conductive rod;
    an insole unit having a first part and a second part which is overlapped on the first part, the conductive unit located between the first part and an inside of the shoe, a through hole defined through the first part and the at least one conductive rod extending through the through hole, and
    a frequency current generating unit having two plugs, a frequency current generating member and two second wires connected between the two plugs and the frequency current generating member, the frequency current generating member is received in the pocket and electrically connected to the conductive unit.

11. The assembly as claimed in claim 10, wherein the frequency current generating unit is controlled by a remote control.

* * * * *